United States Patent [19]
Hrdlicka et al.

[11] Patent Number: 5,443,486
[45] Date of Patent: Aug. 22, 1995

[54] METHOD AND APPARATUS TO LIMIT CONTROL OF PARAMETERS OF ELECTRICAL TISSUE STIMULATORS

[75] Inventors: Gregory A. Hrdlicka, Plymouth; David L. Thompson, Fridley, both of Minn.

[73] Assignee: Medtronic, Inc., Minneapolis, Minn.

[21] Appl. No.: 312,340

[22] Filed: Sep. 26, 1994

[51] Int. Cl.⁶ ............................................. A61N 1/32
[52] U.S. Cl. ..................................... 607/59; 607/117; 607/148
[58] Field of Search ................... 607/30, 2, 46, 62, 63, 607/72, 148, 117, 59, 60

[56] References Cited

U.S. PATENT DOCUMENTS

| | | | |
|---|---|---|---|
| 4,520,825 | 6/1985 | Thompson et al. | 128/422 |
| 5,058,605 | 10/1991 | Slovak | 607/72 |
| 5,159,926 | 11/1992 | Ljungstroem | 607/30 |
| 5,184,617 | 2/1993 | Harris et al. | 607/63 |

*Primary Examiner*—George Manuel
*Attorney, Agent, or Firm*—Terry L. Wiles; Harold R. Patton

[57] ABSTRACT

Electrical tissue stimulator and method for limiting the programmability of stimulation pulse parameters. The tissue stimulator includes a plurality of electrodes and a memory for holding a stimulation pulse parameter limit value and a programmed parameter value of a stimulation pulse. A pulse generator applies electrical stimulation pulses to the electrodes in accordance with the programmed parameter value. Programming means is included for receiving remotely generated programming signals and altering the contents of the memory in accordance with the signals. Means is included for comparing the stimulation pulse parameter limit value and the programmed parameter value and for preventing an alteration of the programmed parameter value, unless it is within stimulation pulse parameter limits. The stimulation pulse parameters may include pulse amplitude, pulse width, and pulse rate and the programmed parameter limit values may be upper and lower limits.

44 Claims, 4 Drawing Sheets

METHOD AND APPARATUS TO LIMIT CONTROL OF PARAMETERS OF ELECTRICAL TISSUE STIMULATORS

FIELD OF THE INVENTION

The invention pertains to the field of electrical tissue stimulators, used in the field of medicine for the treatment of pain. In particular, the invention pertains to limiting the control of programmable parameters by a patient operated programmer.

BACKGROUND OF THE PRIOR ART

Tissue stimulators have gained wide acceptance in the field of medicine for the treatment of chronic, intractable pain. Generally, tissue stimulators include electrical circuits for generating electrical stimulation pulses, electrodes for attaching to the affected part of the body, and leads for conveying the stimulation pulses from the generating circuits to the electrodes. In some cases the entire tissue stimulator system is intended to be implanted within the body while in other cases the pulse generating circuitry is contained in a package external to the body. In this later case of transcutaneous stimulators, electrodes having a significant surface area are held in contact with the skin by adhesives or other means over the affected areas. Another type of stimulation which can be used either with external or implanted pulse generators uses leads extending to an implanted electrode, for example one implanted along the spinal cord. In any case, the application of the electrical stimulation pulses to body tissue produces the effect of relieving or masking the sensation of pain. In more sophisticated units, device controls or RF programming may be provided to turn on or off and/or adjust parameters of the output stimulation such as pulse width, pulse amplitude and repetition rate. Many tissue stimulator pulse generators also provide a burst or cycle mode wherein groups of stimulating pulses are provided at intervals, with delay intervals between the groups. An example of such a commercially available implantable device is the Medtronic Itrel II, Model 7424. This device is substantially described in U.S. Pat. No. 4,520,825, issued Jun. 4, 1985, to Thompson, et al. The Thompson '825 patent describes a circuit implementation of a cyclic gradual turn-on, or ramping of the output amplitude, of a programmable tissue stimulator. The implementation contains separate memory cells for programming the output amplitude and number of pulses at each increasing output level or "step."

In devices of this type, it is desirable to provide some means of control over the amplitude, or intensity, the frequency and the width of the stimulating pulses so that the patient using the device can adjust the device for maximum effectiveness. For example, if the amplitude is too low, them may be insufficient relief and if the amplitude is too high, there can be an unpleasant stinging or tingling sensation. The optimum stimulation parameters may change according to the time since implant and/or a variety of operating conditions including the length of time the stimulation has been on, patient postural changes, patient activity or the like.

Existing patient operated or "take home" programmers or transmitters for implantable tissue stimulators like the Medtronic Itrel II, Model 7424 or a transcutaneous tissue stimulator like the Medtronic Xtrel, Model 3470 have internal switches or controls that enable limiting of patient control over parameters and/or range of operation of selected parameters. Often times patients tamper with the limit setting switches thus causing subsequent lack of proper function. Additionally, during normal battery replacement, memory contents are lost requiring returning to the physician's office for proper resetting. An alternative method of programmer/transmitter parameter control limits would make use of a replaceable IC memory such as a Programmed Read Only Memory (PROM). However this method would severely limit the optimization of parameters for each patient as typical values would have to be preselected, fabricated and inventoried in each physician's office.

SUMMARY OF THE INVENTION

To overcome these and other problems, this invention provides improved circuitry for the control of electrical pulse generation in a tissue stimulator system. The invention is particularly adapted to implantable tissue stimulators, but is also usable in external stimulators. The invention provides circuitry which controls the increase or decrease in pulse amplitude, frequency or width of the stimulation pulses. This permits optimum control over pulse characteristics for the most effective pain relief for the patient, and convenient adjustment to new output pulse parameters as it becomes necessary or desirable from time to time.

In one embodiment the invention is an electrical tissue stimulator which comprises a plurality of electrodes to be implanted in a patient. The stimulator has a first memory for holding a stimulation pulse parameter limit value and a second memory for holding a programmed parameter value of a stimulation pulse. A pulse generator applies electrical stimulation pulses to the electrodes in accordance with the programmed parameter value. The stimulator includes programming means for receiving remotely generated programming signals which is effective to alter the contents (numerical values) of the first or second memories in accordance with the signals received. Means is included for comparing the stimulation pulse parameter limit value and the programmed parameter value and for preventing the programming means from increasing the programmed parameter value, unless the programmed parameter value is less than the stimulation pulse parameter limit value. In another embodiment the comparing means is effective to prevent the programming means from decreasing the programmed parameter value, unless the programmed parameter value is greater than the stimulation pulse parameter limit value.

The stimulator may include means to detect remotely generated programmed parameter value increase signals which cause the programming means to increase the programmed parameter value. Similarly, the stimulator may include means to detect remotely generated programmed parameter value decrease signals in response to which the programming means is effective to decrease the programmed parameter value.

The stimulation pulse parameter limit value contained in the first memory may be an upper pulse parameter limit value, and the stimulator may include a third memory for holding a lower pulse parameter limit value. In this embodiment the contents of the third memory are alterable by the programming means in accordance with remotely generated programming signals.

The tissue stimulator may include additional memories for holding multiple stimulation pulse parameter values and multiple stimulation pulse parameter limit values. The parameters may include pulse amplitude, pulse rate and pulse width. Thus, in one embodiment the electrical tissue stimulator comprises a plurality of electrodes to be implanted in a patient together with a pulse rate memory, a pulse width memory, and a pulse amplitude memory. The pulse rate memory holds upper and lower stimulation pulse rate limit values and a first programmed pulse rate value of a stimulation pulse. Similarly, the pulse width memory and pulse amplitude memory hold upper and lower stimulation pulse width and amplitude limit values and first programmed pulse width and pulse amplitude values, respectively. The stimulator includes a pulse generator for applying electrical stimulation pulses to the electrodes in accordance with the first programmed pulse rate, pulse width, and pulse amplitude values. Programming means are provided for receiving remotely generated programming signals and altering the contents of at least one of the memories in accordance with the signals to permit pulse rate, pulse width, and pulse amplitude upper and lower limit values and first programmed pulse rate, pulse width, and pulse amplitude values to be remotely programmed. Means is included for comparing the pulse rate, pulse width, and pulse amplitude upper and lower limit values with the first programmed pulse rate, pulse width, and pulse amplitude values and for preventing the programming means from increasing the first programmed pulse rate value unless the programmed pulse rate value is less than the upper stimulation pulse rate limit value and from decreasing the first programmed pulse rate value, unless the programmed pulse rate value is greater than the lower stimulation pulse rate limit value. Similarly, the programming means is prevented from increasing and decreasing the first programmed pulse width and pulse amplitude based upon a similar comparison.

In another aspect the invention is a method of limiting the programmability of a stimulation pulse parameter of an implantable tissue stimulator. In one embodiment the method comprises programming a first memory with a stimulation pulse parameter limit value and programming a second memory with a stimulation pulse parameter value. The method further includes receiving remotely generated programming signals and altering the contents of at least one of the memories in accordance with the programming signals. The stimulation pulse parameter limit value and the stimulation pulse parameter value are compared and the method includes limiting the alteration of the contents of the second memory by preventing the increase of the stimulation pulse parameter value, unless the stimulation pulse parameter value is less than the stimulation pulse parameter limit value. In another embodiment the limiting step includes preventing the decrease of the stimulation pulse parameter value, unless the stimulation pulse parameter value is greater than the stimulation pulse parameter limit value.

The stimulation pulse parameter limit values may include an upper stimulation pulse parameter limit value and a lower stimulation pulse parameter limit value. The method may include programming one or more memories with additional stimulation pulse parameter values and additional stimulation pulse parameter limit values. The stimulation pulse parameter values and limit values may include stimulation pulse amplitude, pulse rate, and pulse width.

In one embodiment the invention is a method of controlling the programmability of stimulation pulse parameters of an implantable electrical tissue stimulator comprising programming a pulse rate memory with upper and lower stimulation pulse rate limit values and a first programmed pulse rate value. The method further includes programming a pulse width memory with upper and lower stimulation pulse width limit values and a first programmed pulse width value and programming a pulse amplitude memory with upper and lower stimulation pulse amplitude limit values and a first programmed pulse amplitude value. The method includes receiving remotely generated programming signals and altering the contents of at least one of the memories in accordance with the remotely generated signals. The method includes comparing the pulse rate, pulse width, and pulse amplitude limit values with the first programmed pulse rate, pulse width, and pulse amplitude values, respectively, and preventing the increase of the first programmed pulse rate value, unless the first programmed pulse rate value is less than the upper stimulation pulse rate limit value and preventing the decrease of the first programmed pulse rate value, unless the first programmed pulse rate value is greater than the lower stimulation pulse rate limit value, further preventing the increase of the first programmed pulse width value, unless the first programmed pulse width value is less than the upper stimulation pulse width limit value and preventing the decrease of the first programmed pulse width value, unless the first programmed pulse width value is greater than the lower stimulation pulse width limit value and preventing the increase of the first programmed pulse amplitude value, unless the first programmed pulse amplitude value is less than the upper stimulation pulse amplitude limit value and preventing the decrease of the first programmed pulse amplitude value unless the first programmed pulse amplitude value is greater than the lower stimulation pulse amplitude limit value.

BRIEF DESCRIPTION OF THE DRAWINGS

The features of the present invention which are believed to be novel are set forth with particularity in the appended claims. The invention, together with further objects and advantages thereof, may best be understood by making reference to the following description taken in conjunction with the accompanying drawing, in the several figures of which like reference numerals identify identical elements, and wherein:

FIG. 1b shows a programmer utilized to limit control of stimulation parameters of the tissue stimulator of FIG. 1a.

FIG. 1c shows a patient utilizing a handheld programmer to adjust the stimulation parameters of the programmable tissue stimulator of FIG. 1a.;

FIG. 2 is a schematic block diagram of the programmable tissue stimulator of FIG. 1a;

FIG. 3 is a partial, more detailed schematic block diagram of the programmable tissue stimulator of FIG. 1a.

DETAILED DESCRIPTION OF THE PREFERRED EMBODIMENT

Figure 1A:
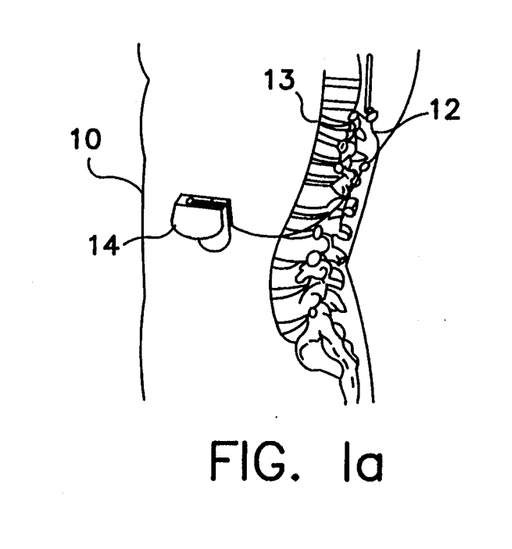
FIG. 1a depicts a programmable tissue stimulator in accordance with the present invention implanted in a patient.
Figure 1B:
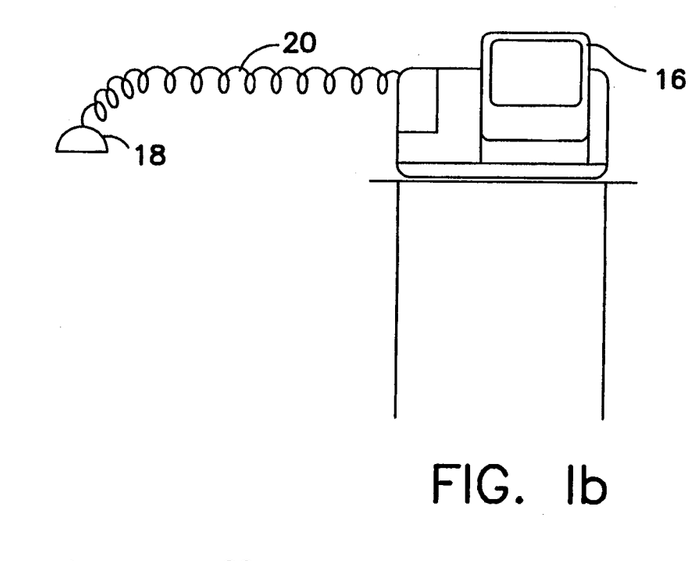
Figure 1C:
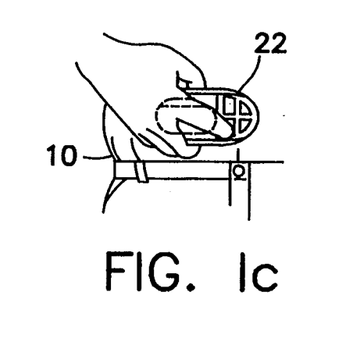

FIG. 1a shows a programmable tissue stimulator 14 which may be implanted in the abdomen of a patient 10 for control of intractable pain. The stimulator 14 is typically connected to a lead system 12 often consisting of an extender (not shown) and a multielectrode lead which is shown implanted adjacent the spinal column 13 of patient 10. Those of skill in the art will appreciate that the position of stimulator 14 and placement of lead system 12 will depend upon the location of the tissue being stimulated. Modifying parameters of stimulator 14 after implantation is typically performed by a physician using a physician programmer 16 as shown in FIG. 1b. RF signals are transmitted to stimulator 14 by a remote programming head 18 connected to programmer 16 via a coiled, stretchable cable 20. Programmer 16 is typically used by the physician to modify operating parameters or, alternatively, interrogate stimulator 14 for the telemetric uplink of various data or status information. Additionally, as shown in FIG. 1c, patients are often sent home with a small handheld battery operated programmer 22 to turn stimulator 14 on or off, or adjust other parameters such as pulse rate, pulse width and/or pulse amplitude as desired.

Figure 2:
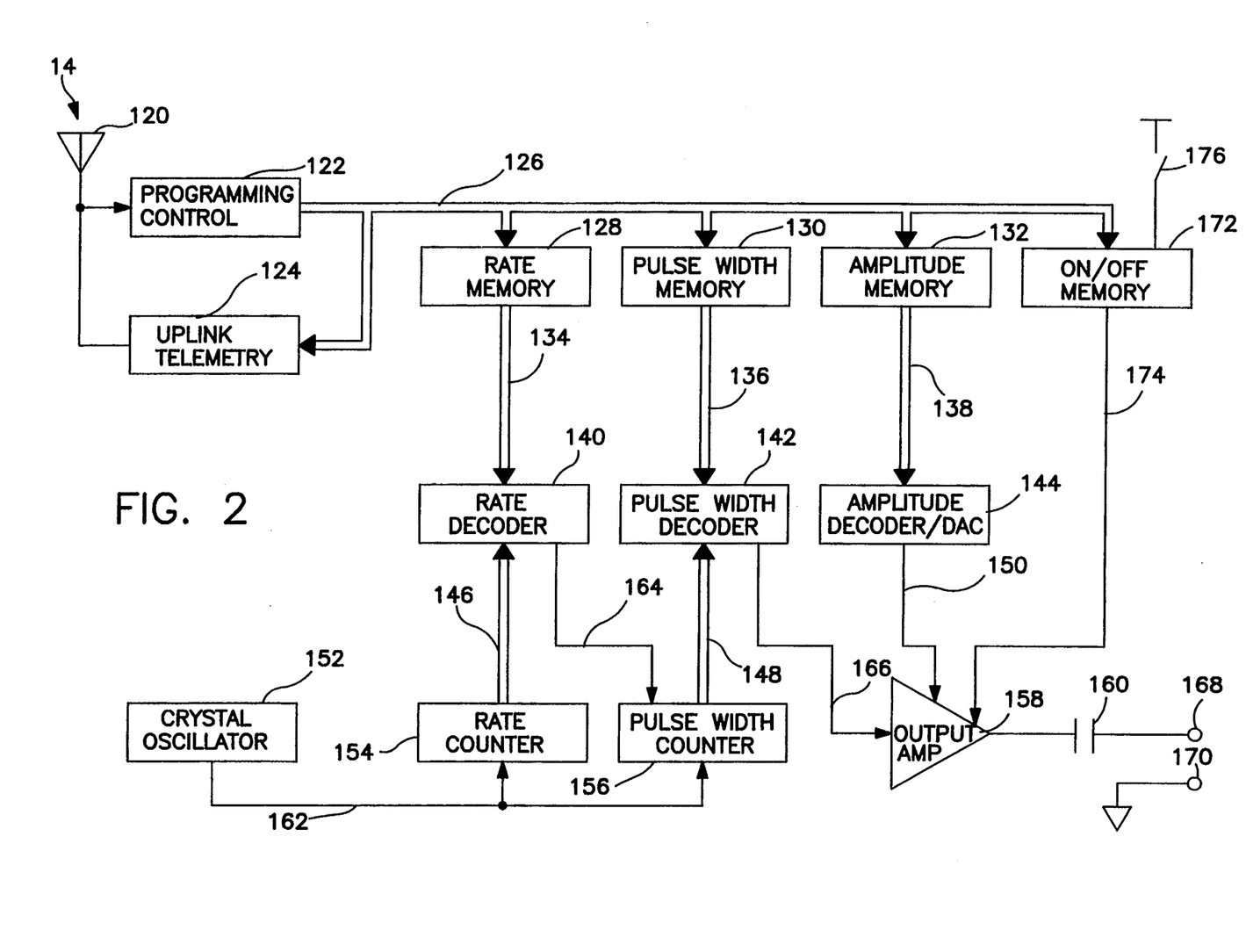

The programmable tissue stimulator 14 shown in block diagram in FIG. 2 is intended to be fully implantable. The programming takes place by means of coded programming signals transmitted from without the body which are received by suitable receiving and decoding circuitry within the implanted stimulator. The coded programming signals are received by a programming control circuit 122 via antenna 120. Programming control circuit 122 includes a receiver, control circuitry therefor, and decoding circuits. Control circuit 122 checks the validity of received signals, decodes them and applies them over data bus network 126 to rate memory 128, pulse width memory 130, amplitude memory 132 and ON/OFF memory 172, as explained more fully below. Various types of systems are known in the art for transmission, reception and decoding of programming signals in implanted devices, and therefore, the circuitry in programming control circuit 122 is not shown in detail. This invention is preferably used with the particular type of programming signal receiver and control set forth in the commonly assigned U.S. Pat. No. 4,676,248, "Circuit for Controlling a Receiver in an Implanted Device" by Berntson, although other types of programming receivers and controls could also be used.

Data bus network 126 is provided for transmitting the program information from control circuit 122 to the various memories. Data bus 126 may take the form of serial or parallel data paths as is generally known in the art. Suitable addressing techniques are used in conjunction with Data Bus 126 to ensure that the appropriate programming information is transmitted to the correct memory location.

ON-OFF memory 172 is connected to the data bus 126 for receiving programming signals indicative of the selected status of the stimulator, i.e., on or off. In addition, a magnetic reed switch 176 is provided within the device and is also connected to memory 172. Reed switch 176 is actuated in the conventional manner by placing an external magnet over the site where the unit is implanted. The status of memory 172, and hence the on or off status of the stimulator, can be controlled either by external programming signals or by applying the magnet externally over the site of the implanted stimulator. The status of memory 172 is communicated over conductor 174 which enables or disables output amplifier 158 depending upon the status of memory 172.

Pulse rate memory 128 consists of a counter or registers connected to data bus 126 to receive and store digital data corresponding to the selected pulse rate. The data content of memory 128 is applied over data bus 134 to an input of rate decoder 140, discussed further below.

Pulse width memory 130 consists of a counter or registers connected to data bus 126 to receive and store digital data corresponding to the selected pulse width. The data contents of memory 130 are applied by data bus 136 to an input of a pulse width decoder 142.

Amplitude memory 132 consists of a counter or registers connected to data bus 126 to receive and store digital data corresponding to the selected amplitude for the output stimulation pulses. The data contents of memory 132 are applied by data bus 138 to an amplitude decoder and digital-to-analog converter (DAC) 144.

As an example, in a preferred embodiment of stimulator 14, the pulse width is programmable between 0.06 and 0.45 milliseconds. The pulse rate is programmable from 2 to 130 pulses per second. The amplitude is programmable from 0 to 10.5 volts. While the above numeric ranges are used in the preferred embodiment, they do not represent limits for the practice of the invention, because through suitable design changes, the ranges listed above could be expanded or narrowed as desired. Also, while the magnitude of output pulses is controlled in terms of voltage in the preferred embodiment, the invention may be employed equally as well to the situation where output pulses are sought to be controlled in terms of current. Lastly, other programmable parameters may be programmed in a typical tissue stimulator as is well known in the art.

Continuing with FIG. 2, timing signals are provided by a reference crystal oscillator 152, typically at 32,768 Hz. Conductor 162 connects the oscillator signal to the input of the rate counter 154 and the pulse width counter 156. The count accumulated in rate counter 154 is output over data bus 146 to rate decoder 140 and a logic signal indicative of a match between the rate memory 128 and the count of counter 156 is conveyed by conductor 164 to the enable input of pulse width counter 156. Upon being enabled, the pulse width counter 156 begins counting clock signals from crystal oscillator 152 until a match between the pulse width memory 130 and the count accumulated in pulse width counter 156 is determined by pulse width decoder 142.

The above process then repeats with the result that pulses are produced on lead 166 having a width corresponding to the preselected pulse width in memory 130, and occurring at a repetition rate corresponding to the preselected rate in memory 128. These pulses cause analog output circuit 158 to produce output stimulation pulses through output capacitor 160 to the lead system at terminals 168 and 170. These stimulation pulses are carried by leads (not shown) to electrodes (also not shown) to provide electrical tissue stimulation. The output pulses occur at times controlled by the occurrence of pulses at conductor 166 and they last for a duration controlled by the duration of the pulses at conductor 166. However, the amplitude of the output pulses is controlled by the analog signal at conductor 150 and enabled and disabled by the signal on conductor 174 from the ON/OFF memory 172. ON/OFF memory 172 is controlled via signals from external Programmer 16 or 22 or from closure of reed switch 176 as is well known in the art.

Figure 3:
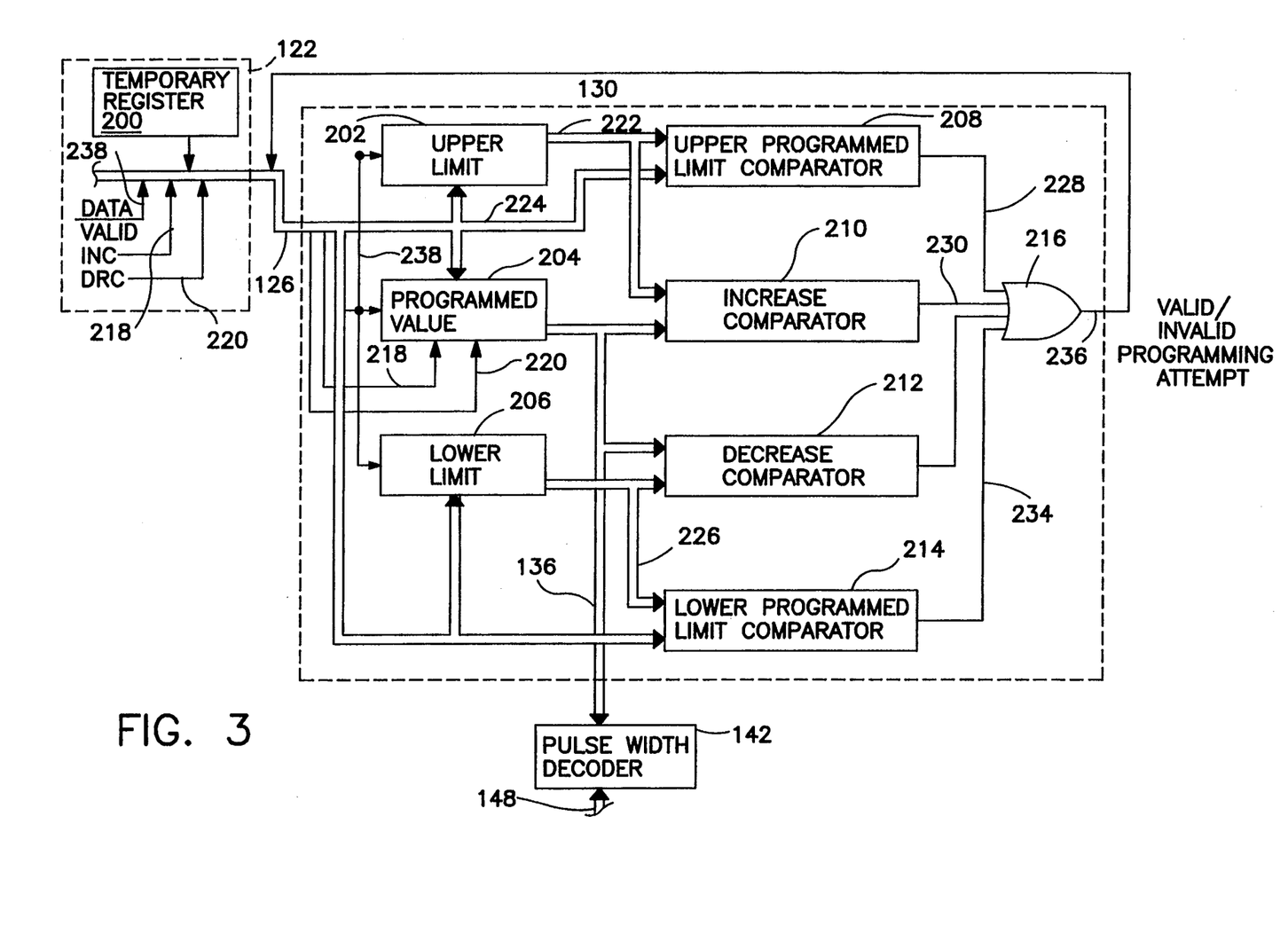

Turning to FIG. 3, the present invention is shown in more detail. The pulse circuitry and operation of pulse width memory will be described in detail. The circuitry and operation of rate memory 128 and pulse amplitude memory 132 are similar and need not be described in order to understand the present invention.

The pulse width memory 130 consists of three registers, or memories; upper limit 202, programmed value 204 and lower limit 206. All three are connected to programming control circuit 122 and uplink telemetry 124 (from FIG. 2) through data bus 224 and data bus 126. A temporary register 200 in control circuit 122 holds the current downlink telemetry data until data valid control 238 from control circuit 122 allows transfer of temporary data held in temporary register 200 to one or more of the upper limit 202, programmed value 204 or lower limit 206 registers.

Upper programmed limit comparitor 208 is connected to the upper limit register 202 via data bus 222 and to the temporary register 200 via data bus 224 and data bus 126. Upper programmed limit comparitor 208 compares the values in the temporary register 200 to the upper limit register 202 to ensure that the new programmed value stored in temporary register 200 is less than, or equal to, the value previously stored in the upper limit register 202. A signal indicative of this comparison is output from the upper programmed limit comparitor 208 via signal line 228 to valid/invalid OR gate 216. The output of valid/invalid OR gate 216 is output via signal line 236 to control circuit 122. If the value in temporary register 200 is less than, or equal to, the upper limit register 202, a valid programming attempt is recognized, and control circuit 122 transfers data from the temporary register 200 to the programmed value register 204. If an invalid value is detected, no data is transferred, the current data value in the programmed value register 204 remains and the invalid data in the temporary register 200 is cleared.

Lower programmed limit comparitor 214 is connected to the lower limit register 206 via data bus 226 and to the temporary register 200 via data bus 224. Lower programmed limit comparitor 214 compares the values in the temporary register 200 to the lower limit register 206 to ensure that the new programmed value stored in the temporary register 200 is greater than, or equal to, the value previously stored in the lower limit register 206. A signal indicative of this comparison is output from the lower programmed limit comparitor 214 via signal line 234 to valid/invalid OR gate 216. The output of valid/invalid OR gate 216 is output via signal line 236 to control circuit 122. If the value in temporary register 200 is greater than, or equal to, the lower limit register 206, a valid programming attempt is recognized and control circuit 122 transfers data from the temporary register 200 to the programmed value register 204 as herein above described. If an invalid value is detected, no data is transferred, the current data value in the programmed value register 204 remains and the invalid data in the temporary register 200 is cleared also as herein above described.

Increase comparitor 210 is connected to the upper limit register 202 via data bus 222 and to the programmed value register 204 via data bus 136. Increase comparitor 210 compares the values in the programmed value register 204 to the upper limit register 202 to insure that an increase command via INC line 218 which may be received from the patient operated hand-held programmer 22 does not cause the programmed value 204 to exceed the value in the upper limit register 202. A signal indicative of this comparison is output from the increase comparitor 210 via signal line 230 to valid/invalid OR gate 216. The output of valid/invalid OR gate 216 is output via signal line 236 to control circuit 122. If the value in the programmed value register 204 is less than the value in the upper limit register 202, a valid programming attempt is recognized and control circuit 122 allows the INC signal line 218 to increase the programmed value register 204 one programmable step via data valid line 238. If an invalid value is detected, the current value in the programmed value register 204 remains and the INC signal line 218 is cleared.

Decrease comparitor 212 is connected to the lower limit register 206 via data bus 226 and to the programmed value register 204 via data bus 136. Decrease comparitor 212 compares the values in the programmed value register 204 to the lower limit register 206 to ensure that a decrease command via DRC line 220 which may be received from the patient operated hand-held programmer 22 does not cause the programmed value 204 to drop below the value in the lower limit register 206. A signal indicative of this comparison is output from the decrease comparitor 212 via signal line 232 to valid/invalid OR gate 216. The output of valid/invalid OR gate 216 is output via signal line 236 to control circuit 122. If the value in the programmed value register 204 is greater than the lower limit register 206, a valid programming attempt is recognized and control circuit 122 allows the DRC signal line 220 to decrease the programmed value register 204 one programmable step via data valid line 238. If an invalid value is detected, the current value in the programmed value register 204 remains and the DRC signal line 220 is cleared.

At implant or subsequent follow-up, the physician may program the rate, pulse width or amplitude memories to any of the selectable values with physician programmer 16 of FIG. 1. Typically, the upper and lower limit memories will be programmed to different values to enable a range of operation of the implanted device 14. Encoded RF signals will be transmitted to the stimulator 14 via antenna 120 to the control circuit 122 where signals are decoded and transferred to the appropriate memory cells; rate 128, pulse width 130 or amplitude 132 as is known in the art. If the physician sets the upper and lower limit values to the same as the programmed value, the parameter will be fixed or not programmable by the patient.

Patient programmer 22 may subsequently be used by the patient to turn on or off the stimulator 14 or to control the operating programmed rate, pulse width or amplitude. The patient does this by holding the programmer 22 over the stimulator implant site and depressing an increase or decrease button located on the programmer. Encoded RF signals will be transmitted to the stimulator 14 via antenna 120 to the control circuit 122 where the signals am decoded and the appropriate memory cell; Rate 128, Pulse Width 130 or Amplitude 132; are incremented or decremented one value respectively. Alternatively, the patient programmer 22 may allow selection of a specific value for the rate, pulse width or amplitude parameter to be transmitted to the implanted stimulator 14.

Figure 4:
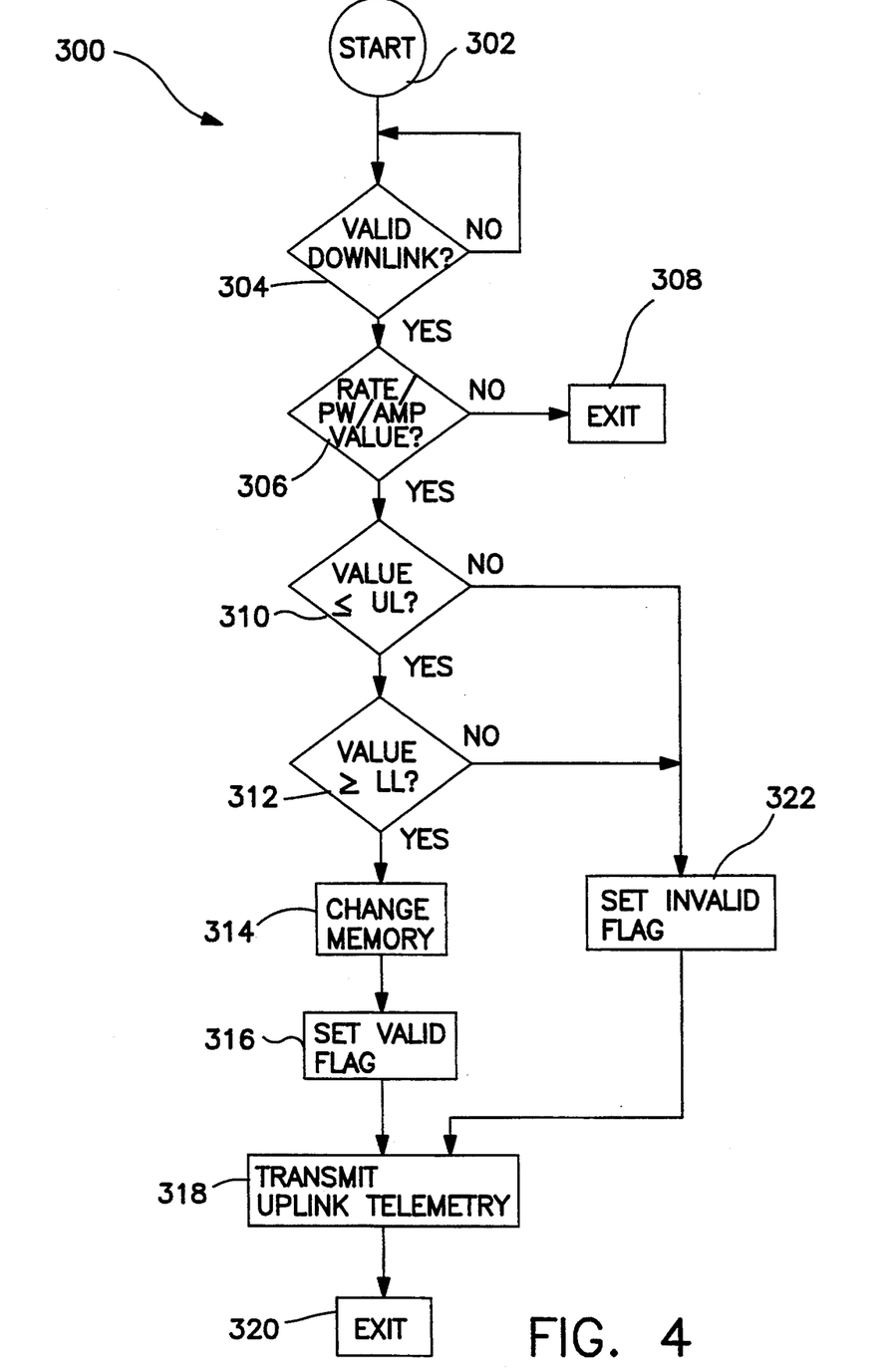
FIG. 4 is a flow diagram of a method of implementation of the present invention.

Turning now to FIG. 4, a flow diagram 300 of the increase/decrease programming of the implanted stimulator 14 via the patient programmer 22 is shown. The flow diagram 300 begins at 302. At block 304, them is a test for valid downlink telemetry. If the downlink telemetry is valid, it is tested for rate, pulse width or pulse amplitude adjustments at 306. If at block 306 rate, pulse width or pulse amplitude are not being programmed, the flow diagram is exited at 308. If, alternatively, at block 306 the answer is yes, the parameter value is tested to determine that it is less than, or equal to the upper limit value at 310. If the parameter value is less than or equal to the programmed upper limit, the parameter value is tested at 312 to determine that it is greater than or equal to the programmed lower limit. If yes, the programmed value is loaded into memory at 314, the valid flag is set at 316, an uplink telemetry confirmation of the change is sent at 318 and the flow diagram is stopped at 320. If, alternatively, at block 310 the new programmed value is not less than, or equal to the programmed upper limit, or at block 312 it is not greater than or equal to the programmed lower limit, the invalid flag is set at 322, an uplink telemetry transmission of this failure is sent at 318 and the flow diagram is exited at 320.

Although the invention described herein is described as a neurological tissue stimulator used in conjunction with an external programmer, it would be useful to implement this concept in other implantable medical devices such as pacemakers, automatic implantable cardioverters/defibrillators, drug pumps, cardiac assist systems and the like. Alternatively, although the herein described invention is shown with 2 limits, an upper and a lower limit, only one limit may be used; for example a maximum or, alternatively, a minimum limit.

What is claimed is:

1. An electrical tissue stimulator comprising:
   a plurality of electrodes to be implanted in a patient;
   a first memory for holding a stimulation pulse parameter limit value of a stimulation pulse;
   a second memory for holding a programmed parameter value of a stimulation pulse;
   a pulse generator for applying electrical stimulation pulses to said electrodes in accordance with said programmed parameter value;
   programming means for receiving remotely generated programming signals and altering the contents of at least one of said first and second memories in accordance with said signals; and
   means for comparing said stimulation pulse parameter limit value and said programmed parameter value and for preventing said programming means from increasing said programmed parameter value unless said programmed parameter value is less than said stimulation pulse parameter limit value.

2. A tissue stimulator according to claim 1 wherein said programming means includes a means to detect remotely generated programmed parameter value increase signals, said programming means being responsive to increase said programmed parameter value upon receipt of said increase signals.

3. A tissue stimulator according to claim 1 wherein the stimulation pulse parameter limit value contained in said first memory is an upper pulse parameter limit value and wherein the stimulator further comprises a third memory for holding a lower pulse parameter limit value, the contents of said third memory being alterable by said programming means in accordance with remotely generated programming signals, and wherein said comparing means compares said upper pulse parameter limit value, said programmed parameter value and said lower pulse parameter limit value and prevents said programming means form increasing said programmed parameter value unless said programmed parameter value is less than said upper pulse parameter limit value and from decreasing said programmed parameter value unless said programmed parameter value is greater that said lower pulse parameter limit value.

4. A tissue stimulator according to claim 3 wherein said programming signals are digital signals.

5. A tissue stimulator according to claim 3 wherein said programming means includes a means to detect remotely generated programmed parameter value increase signals and programmed parameter value decrease signals, said programming means being responsive to increase said programmed parameter value upon receipt of said increase signals and to decrease said programmed parameter value upon receipt of said decrease signals and wherein said comparing means includes means to compare said programmed parameter value to said upper pulse parameter limit value and to said lower pulse parameter limit value and to prevent said programming means from increasing said programmed parameter value unless said programmed parameter value is less than said upper pulse parameter limit and from decreasing said programmed parameter value unless said programmed parameter value is greater than said lower pulse parameter limit value.

6. An electrical tissue stimulator according to claim 1 wherein said stimulation pulse parameter limit value is one of stimulation pulse amplitude limit value, stimulation pulse rate limit value and stimulation pulse width limit value.

7. An electrical tissue stimulator comprising:
   a plurality of electrodes to be implanted in a patient;
   a first memory for holding a stimulation pulse parameter limit value of a stimulation pulse;
   a second memory for holding a programmed parameter value of said stimulation pulse;
   a pulse generator for applying electrical stimulation pulses to said electrodes in accordance with said programmed parameter value;
   programming means for receiving remotely generated programming signals and altering the contents of at least one of said first and second memories in accordance with said signals to permit said stimulation pulse parameter limit value and said programmed parameter value to be remotely programmed; and
   means for comparing said stimulation pulse parameter limit value and said programmed parameter value and for preventing said programming means from decreasing said programmed parameter value unless said programmed parameter value is greater than said stimulation pulse parameter limit value.

8. A tissue stimulator according to claim 7 wherein said programming means includes a means to detect remotely generated programmed parameter value decrease signals, said programming means being responsive to decrease said programmed parameter value upon receipt of said decrease signals, and wherein said comparing means includes means to compare said programmed parameter value to said stimulation pulse parameter limit value and to prevent said programming means from decreasing said programmed parameter value unless said programmed parameter value is greater than said stimulation pulse parameter limit value.

9. An electrical tissue stimulator according to claim 7 wherein said stimulation pulse parameter limit value is one of stimulation pulse amplitude limit value, stimulation pulse rate limit value and stimulation pulse width limit value.

10. An electrical tissue stimulator comprising:
   a plurality of electrodes to be implanted in a patient;
   a first memory for holding a first stimulation pulse parameter limit value of a stimulation pulse and a first programmed parameter value of said stimulation pulse;
   a pulse generator for applying electrical stimulation pulses to said electrodes in accordance with said first programmed parameter value;
   programming means for receiving remotely generated programming signals and altering the contents of said first memory in accordance with said signals to permit said first parameter limit value and said first programmed parameter value to be remotely programmed; and
   means for comparing said first parameter limit value and said first programmed parameter value and for preventing said programming means from increasing said first programmed parameter value unless said first programmed parameter value is less than said first parameter limit value.

11. An electrical tissue stimulator according to claim 10 further comprising a second memory for holding a second stimulation pulse parameter limit value of a stimulation pulse and a second programmed parameter value of said stimulation pulse, and wherein said pulse generator applies stimulation pulses to said electrodes in accordance with said first and second programmed parameter values, the contents of said second memory being alterable by said programming means in accordance with said remotely generated programming signals, and wherein said means for comparing compares said second parameter limit value and said second programmed parameter value and prevents said programming means form increasing said second programmed parameter value unless said second programmed parameter value is less than said second parameter limit value.

12. An electrical tissue stimulator according to claim 11 further comprising a third memory for holding a third stimulation pulse parameter limit value of a stimulation pulse and a third programmed parameter value of said stimulation pulse, and wherein said pulse generator applies stimulation pulses to said electrodes in accordance with said first, second and third programmed parameter values, the contents of said third memory being alterable by said programming means in accordance with said remotely generated programming signals, and wherein said means for comparing compares said third parameter limit value and said third programmed parameter value and prevents said programming means from increasing said third programmed parameter value unless said third programmed parameter value is less than said third parameter limit value.

13. An electrical tissue stimulator according to claim 12 wherein the first, second and third stimulation pulse parameter limit values contained in said first, second and third memories each comprise an upper pulse parameter limit value and a lower pulse parameter limit value, and wherein said comparing means compares said first parameter limit value to said first programmed parameter value, said second parameter limit value to said second programmed parameter value and said third parameter limit value to said third programmed parameter value and prevents said programming means from increasing the value of said first programmed parameter value unless said first programmed parameter value is less than said upper parameter limit value and from decreasing the value of said first programmed parameter value unless said first programmed parameter value is greater than said lower parameter limit value of said first stimulation pulse parameter limit value, from increasing the value of said second programmed parameter value unless said second programmed parameter value is less than said upper parameter limit value and from decreasing the value of said second programmed parameter value unless said second programmed parameter value is greater than said lower parameter limit value of said second stimulation pulse parameter limit value, and from increasing the value of said third programmed parameter value unless said third programmed parameter value is less than said upper parameter limit value and from decreasing the value of said third programmed parameter value unless said third programmed parameter value is greater than said lower parameter limit value of said third stimulation pulse parameter limit value.

14. A tissue stimulator according to claim 13 wherein said programming means includes a means to detect remotely generated first, second and third programmed parameter value increase signals and first, second and third programmed parameter value decrease signals, said programming means being responsive to increase said first programmed parameter value upon receipt of said first programmed parameter increase signals and to decrease said first programmed parameter value upon receipt of said first programmed parameter decrease signals, said programming means being further responsive to increase said second programmed parameter value upon receipt of said second programmed parameter increase signals and to decrease said second programmed parameter value upon receipt of said second programmed parameter decrease signals, said programming means being further responsive to increase said third programmed parameter value upon receipt of said third programmed parameter increase signals and to decrease said third programmed parameter value upon receipt of said third programmed parameter decrease signals.

15. A tissue stimulator according to claim 12 wherein said programming means includes means to detect remotely generated first, second and third programmed parameter value increase signals, said programming means being responsive to increase said first programmed parameter value upon receipt of said first programmed parameter increase signals, to increase said second programmed parameter value upon receipt of said second programmed parameter increase signals, and to increase said third parameter value upon receipt of said third parameter value increase signals.

16. An electrical tissue stimulator according to claim 11 wherein said first and second stimulation pulse parameter limit values contained in said first and second memories each comprise an upper pulse parameter limit value and a lower pulse parameter limit value, and wherein said comparing means compares said first parameter limit value to said first programmed parameter value and said second parameter limit value to said second programmed parameter value and prevents said programming means from increasing the value of said first programmed parameter value unless said first programmed parameter value is less than said upper parameter limit value and from decreasing the value of said first programmed parameter value unless said first programmed parameter value is greater than said lower parameter limit value of said first stimulation pulse parameter limit value and further prevents said programming means from increasing the value of said second programmed parameter value unless said second programmed parameter value is less than said upper parameter limit value and from decreasing the value of said second programmed parameter value unless said second programmed parameter value is greater than said lower parameter limit value of said second stimulation pulse parameter limit value.

17. A tissue stimulator according to claim 16 wherein said programming means includes a means to detect remotely generated first and second programmed parameter value increase signals and first and second programmed parameter value decrease signals, said programming means being responsive to increase said first programmed parameter value upon receipt of said first programmed parameter increase signals and to decrease said first programmed parameter value upon receipt of said first programmed parameter decrease signals, said programming means being further responsive to increase said second programmed parameter value upon receipt of said second programmed parameter increase signals and to decrease said second programmed parameter value upon receipt of said second programmed parameter decrease signals.

18. A tissue stimulator according to claim 11 wherein said programming means includes means to detect remotely generated first and second programmed parameter value increase signals, said programming means being responsive to increase said first programmed parameter value upon receipt of said first programmed parameter increase signals, said programming means being further responsive to increase said second programmed parameter value upon receipt of said second programmed parameter increase signals.

19. An electrical tissue stimulator according to claim 10 wherein said first stimulation pulse parameter limit value contained in said first memory comprises an upper pulse parameter limit value and a lower pulse parameter limit value and wherein said comparing means compares said upper pulse parameter limit value, said first programmed parameter value and said lower pulse parameter limit value and prevents said programming means from increasing said first programmed parameter value unless said first programmed value is less than said upper parameter limit value and from decreasing the value of said first programmed parameter value unless said first programmed parameter value is greater than said lower parameter limit value.

20. A tissue stimulator according to claim 19 wherein said programming means includes a means to detect remotely generated first programmed parameter value increase signals and first programmed parameter value decrease signals, said programming means being responsive to increase said first programmed parameter value upon receipt of said first programmed parameter increase signals and to decrease said first programmed parameter value upon receipt of said first programmed parameter decrease signals.

21. A tissue stimulator according to claim 10 wherein said programming means includes a means to detect remotely generated programmed parameter value increase signals, said programming means being responsive to increase said first programmed parameter value upon receipt of said increase signals.

22. An electrical tissue stimulator comprising:
a plurality of electrodes to be implanted in a patient;
a pulse rate memory for holding upper and lower stimulation pulse rate limit values of a stimulation pulse and a first programmed pulse rate value of said stimulation pulse;
a pulse width memory for holding upper and lower stimulation pulse width limit values of a stimulation pulse and a first programmed pulse width value of said stimulation pulse;
a pulse amplitude memory for holding upper and lower stimulation pulse amplitude limit values of a stimulation pulse and a first programmed pulse amplitude value of said stimulation pulse;
a pulse generator for applying electrical stimulation pulses to said electrodes in accordance with said first programmed pulse rate, pulse width and pulse amplitude values;
programming means for receiving remotely generated programming signals and altering the contents of at least one of said pulse rate, pulse width and pulse amplitude memories in accordance with said signals to permit said pulse rate, pulse width and pulse amplitude upper and lower limit values and said first programmed pulse rate, pulse width and pulse amplitude values to be remotely programmed; and
means for comparing said pulse rate, pulse width and pulse amplitude upper and lower limit values with said first programmed pulse rate, pulse width and pulse amplitude values and for preventing said programming means from increasing said first programmed pulse rate value unless said programmed pulse rate value is less than said upper stimulation pulse rate limit value and from decreasing said first programmed pulse rate value unless said programmed pulse rate value is greater than said lower stimulation pulse rate limit value, for preventing said programming means from increasing said first programmed pulse width value unless said first programmed pulse width value is less than said upper stimulation pulse width limit value and from decreasing said first programmed pulse width value unless said first programmed pulse width value is greater than said lower stimulation pulse width limit value, and for preventing said programming means from increasing said first programmed pulse amplitude value unless said first programmed pulse amplitude value is less than said upper stimulation pulse amplitude limit value and from decreasing said first programmed pulse amplitude value unless said first programmed pulse amplitude value is greater than said lower stimulation pulse amplitude limit value.

23. A tissue stimulator according to claim 22 wherein said programming means includes a means to detect remotely generated pulse rate, pulse width and pulse amplitude value increase and decrease signals, said programming means being responsive to increase said first programmed pulse rate value upon receipt of said pulse rate increase signals and to decrease said first programmed pulse rate value upon receipt of said pulse rate decrease signals, said programming means being further responsive to increase said first programmed pulse width value upon receipt of said pulse width increase signals and to decrease said first programmed pulse width value upon receipt of said pulse width decrease signals, said programming means being further responsive to increase said first programmed pulse amplitude value upon receipt of said pulse amplitude increase signals and to decrease said first programmed pulse amplitude value upon receipt of said pulse amplitude decrease signals.

24. A method of limiting the programmability of a stimulation pulse parameter of an implantable tissue stimulator comprising:

programming a first memory with a stimulation pulse parameter limit value;
programming a second memory with a stimulation pulse parameter value;
receiving remotely generated programming signals;
altering the contents of at least one of said first and second memories in accordance with said programming signals;
comparing said stimulation pulse parameter limit value and said stimulation pulse parameter value; and
limiting the alteration of the contents of said second memory by preventing the increase of said stimulation pulse parameter value unless said stimulation pulse parameter value is less than said stimulation pulse parameter limit value.

25. A method according to claim 24 wherein the remotely generated programming signals include parameter value increase signals and wherein the altering step includes increasing said stimulation pulse parameter value upon receipt of said increase signals.

26. A method according to claim 24 wherein the stimulation pulse parameter limit value contained in said first memory is an upper pulse parameter limit value and wherein the method further comprises programming a third memory with a lower pulse parameter limit value and altering the contents of said third memory in accordance with said remotely generated programming signals, and wherein the comparing step includes comparing said upper pulse parameter limit value, said stimulation pulse parameter value and said lower pulse parameter limit value, the method further including limiting the alteration of the contents of said second memory by preventing the increase of said stimulation pulse parameter value unless said stimulation pulse parameter value is less than said upper pulse parameter limit value and by preventing the decrease of said stimulation pulse parameter value unless said stimulation pulse parameter value is greater than said lower pulse parameter limit value.

27. A method according to claim 26 wherein the remotely generated programming signals include parameter value increase signals and parameter value decrease signals, and wherein the altering step includes increasing said stimulation pulse parameter value upon receipt of said increase signals and decreasing said stimulation pulse parameter value upon receipt of said decrease signals.

28. A method according to claim 24 wherein said stimulation pulse parameter limit value is one of stimulation pulse amplitude limit value, stimulation pulse rate limit value and stimulation pulse width limit value.

29. A method of limiting the programmability of a stimulation pulse parameter of an implantable tissue stimulator comprising:

programming a first memory with a stimulation pulse parameter limit value;
programming a second memory with a stimulation pulse parameter value;
receiving remotely generated programming signals;
altering the contents of at least one of said first and second memories in accordance with said programming signals;
comparing said stimulation pulse parameter limit value and said stimulation pulse parameter value; and
limiting the alteration of the contents of said second memory by preventing the decrease of said stimulation pulse parameter value unless said stimulation pulse parameter value is greater than said stimulation pulse parameter limit value.

30. A method according to claim 29 wherein the remotely generated programming signals include parameter value decrease signals and wherein the altering step includes decreasing said stimulation pulse parameter value upon receipt of said decrease signals.

31. A method according to claim 29 wherein said stimulation pulse parameter limit value is one of stimulation pulse amplitude limit value, stimulation pulse rate limit value and stimulation pulse width limit value.

32. A method of limiting the programmability of a stimulation pulse parameter of an implantable tissue stimulator comprising:

programming a first memory with a first stimulation pulse parameter limit value and a first stimulation pulse parameter value;
receiving remotely generated programming signals;
altering the contents of said first memory in accordance with said programming signals;
comparing said first stimulation pulse parameter limit value and said first stimulation pulse parameter value; and
limiting the alteration of the contents of said first memory by preventing the increase of said stimulation pulse parameter value unless said first stimulation pulse parameter value is less than said first stimulation pulse parameter limit value.

33. A method according to claim 32 further comprising programming a second memory with a second stimulation pulse parameter limit value and a second stimulation pulse parameter value, the method further including altering the contents of said second memory in accordance with said remotely generated programming signals, and wherein the comparing step includes comparing said second stimulation pulse parameter limit value and said second stimulation pulse parameter value and wherein the limiting step includes preventing the increase of said second stimulation pulse parameter value unless said second stimulation pulse parameter value is less than said second stimulation pulse parameter limit value.

34. A method according to claim 33 further comprising programming a third memory with a third stimulation pulse parameter limit value and a third stimulation pulse parameter value, the method further including altering the contents of said third memory in accordance with said remotely generated programming signals, and wherein the comparing step includes comparing said third stimulation pulse parameter limit value and said third stimulation pulse parameter value and wherein the limiting step includes preventing the increase of said third stimulation pulse parameter value unless said third stimulation pulse parameter value is less than said third stimulation pulse parameter limit value.

35. A method according to claim 34 wherein said first, second and third stimulation pulse parameter limit values contained in said first, second and third memories each comprise an upper pulse parameter limit value and a lower pulse parameter limit value, and wherein the comparing step includes comparing the upper and lower pulse parameter limit values of said first stimulation pulse parameter limit value to said first stimulation pulse parameter value, the upper and lower pulse parameter limit values of said second stimulation pulse parameter limit value to said second stimulation pulse parameter value and the upper and lower pulse parameter limit values of said third stimulation pulse parameter limit value to said third stimulation pulse parameter value, and wherein the limiting step includes preventing the increase of the value of said first stimulation pulse parameter value unless said first stimulation pulse parameter value is less than said upper parameter limit value and preventing the decrease of said first stimulation pulse parameter value unless said first stimulation pulse parameter value is greater than said lower parameter limit value of said first stimulation pulse parameter limit value, preventing the increase of the value of said second stimulation pulse parameter value unless said second stimulation pulse parameter value is less than said upper parameter limit value and preventing the decrease of said second stimulation pulse parameter value unless said second stimulation pulse parameter value is greater than said lower parameter limit value of said second stimulation pulse parameter limit value, and preventing the increase of the value of said third stimulation pulse parameter value unless said third stimulation pulse parameter value is less than said upper parameter limit value and preventing the decrease of said third stimulation pulse parameter value unless said third stimulation pulse parameter value is greater than said lower parameter limit value of said third stimulation pulse parameter limit value.

36. A method according to claim 35 wherein said remotely generated programming signals include at least one of first, second and third programmed parameter value increase signals and first, second and third programmed parameter value decrease signals, and wherein said altering step includes increasing said first stimulation pulse parameter value upon receipt of said first programmed parameter increase signals and decreasing said first stimulation pulse parameter value upon receipt of said first programmed parameter decrease signals, said altering step further including increasing said second stimulation pulse parameter value upon receipt of said second programmed parameter value increase signals and decreasing said second stimulation pulse parameter value upon receipt of said second programmed parameter decrease signals, said altering step further including increasing said third stimulation pulse parameter value upon receipt of said third programmed parameter value increase signals and decreasing said third stimulation pulse parameter value upon receipt of said third programmed parameter decrease signals.

37. A method according to claim 34 wherein said remotely generated programming signals include at least one of first, second and third programmed parameter value increase signals, and wherein the altering step includes increasing said first stimulation signal parameter value upon receipt of said first programmed parameter increase signals, increasing said second stimulation pulse parameter value upon receipt of said second programmed parameter increase signals, and increasing said third stimulation pulse parameter value upon receipt of said third programmed parameter increase signals.

38. A method according to claim 33 wherein said first and second stimulation pulse parameter limit values contained in said first and second memories each comprise an upper pulse parameter limit value and a lower pulse parameter limit value and wherein the comparing step includes comparing the upper and lower pulse parameter limit values of said first stimulation pulse parameter limit value to said first programmed parameter value and the upper and lower pulse parameter limit values of said second parameter limit value to said second programmed parameter value and wherein the limiting step includes preventing the increase of the value of said first stimulation pulse parameter value unless said first programmed parameter value is less than said upper parameter limit value and preventing the decrease of the value of said first stimulation pulse parameter value unless said first stimulation pulse parameter value is greater than said lower parameter limit value of said first stimulation pulse parameter limit value and further preventing the increase of the value of said second stimulation pulse parameter value unless said second stimulation pulse parameter value is less than said upper parameter limit value and preventing the decrease of the value of said second stimulation pulse parameter value unless said second stimulation pulse parameter value is greater than said lower parameter limit value of said second stimulation pulse parameter limit value.

39. A method according to claim 38 wherein said remotely generated programming signals include at least one of first and second programmed parameter value increase signals and first and second programmed parameter value decrease signals, and wherein said altering step includes increasing said first stimulation pulse parameter value upon receipt of said first programmed parameter increase signals and decreasing said first stimulation pulse parameter value upon receipt of said first programmed parameter decrease signals, said altering step further including increasing said second stimulation pulse parameter value upon receipt of said second programmed parameter value increase signals and decreasing said second stimulation pulse parameter value upon receipt of said second programmed parameter decrease signals.

40. A method according to claim 33 wherein said remotely generated programming signals include first and second stimulation pulse parameter value increase signals, and wherein the altering step includes increasing said first stimulation pulse parameter value upon receipt of said first stimulation pulse parameter increase signals and increasing said second stimulation pulse parameter value upon receipt of said second stimulation pulse parameter increase signals.

41. A method according to claim 32 wherein the first stimulation pulse parameter limit value contained in said first memory comprises an upper pulse parameter limit value and a lower pulse parameter limit value and wherein the comparing step includes comparing said upper pulse parameter limit value, said first stimulation pulse parameter value and said lower pulse parameter limit value and wherein the limiting step includes preventing the increase of the value of said first stimulation pulse parameter value unless said first stimulation pulse parameter value is less than said upper parameter limit value and preventing the decrease of the value of said first stimulation pulse parameter value unless said first stimulation pulse parameter value is greater than said lower parameter limit value.

42. A method according to claim 41 wherein said remotely generated programming signals include at least one of first programmed parameter value increase signals and first programmed parameter value decrease signals, and wherein the altering step includes increasing said first programmed parameter value upon receipt of said first programmed parameter increase signals and decreasing said first programmed parameter value upon receipt of said first programmed parameter decrease signals.

43. A method according to claim 32 wherein the remotely generated programming signals include parameter value increase signals and wherein the altering step includes increasing said stimulation pulse parameter value upon receipt of said increase signals.

44. A method of controlling the programmability of stimulation pulse parameters of an implantable electrical tissue stimulator comprising:

programming a pulse rate memory with upper and lower stimulation pulse rate limit values of a stimulation pulse and a first programmed pulse rate value of said stimulation pulse;

programming a pulse width memory with upper and lower stimulation pulse width limit values of a stimulation pulse and a first programmed pulse width value of said stimulation pulse;

programming a pulse amplitude memory with upper and lower stimulation pulse amplitude limit values of a stimulation pulse and a first programmed pulse amplitude value of said stimulation pulse;

receiving remotely generated programming signals;

altering the contents of at least one of said pulse rate, pulse width and pulse amplitude memories in accordance with said remotely generated signals; and comparing said pulse rate, pulse width and pulse amplitude limit values with said first programmed pulse rate, pulse width and pulse amplitude values, respectively; and preventing the increase of said first programmed pulse rate value unless the first programmed pulse rate value is less than said upper stimulation pulse rate limit value and preventing the decrease of said first programmed pulse rate value unless said first programmed pulse rate value is greater than said lower stimulation pulse rate limit value, further preventing the increase of said first programmed pulse width value unless said first programmed pulse width value is less than said upper stimulation pulse width limit value and preventing the decrease of said first programmed pulse width value unless said first programmed pulse width value is greater than said lower stimulation pulse width limit value, further preventing the increase of said first programmed pulse amplitude value unless said first programmed pulse amplitude value is less than said upper stimulation pulse amplitude limit value and preventing the decrease of said first programmed pulse amplitude value unless said first programmed pulse amplitude value is greater than said lower stimulation pulse amplitude limit value.

* * * * *